(12) United States Patent
Graziano

(10) Patent No.: US 10,048,209 B2
(45) Date of Patent: *Aug. 14, 2018

(54) STIMULATED EMISSION AND ENHANCED DETECTION OF CHEMICALS AND CHEMICAL COMPOUNDS

(71) Applicant: ALVA LABS, LLC, Marlboro, NJ (US)

(72) Inventor: Richard Graziano, Albion, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/231,790

(22) Filed: Apr. 1, 2014

(65) Prior Publication Data

US 2016/0169804 A1 Jun. 16, 2016

Related U.S. Application Data

(63) Continuation-in-part of application No. 13/585,322, filed on Aug. 14, 2012, now Pat. No. 8,686,366, which is a continuation of application No. 12/344,246, filed on Dec. 25, 2008, now Pat. No. 8,242,450.

(60) Provisional application No. 61/016,756, filed on Dec. 26, 2007.

(51) Int. Cl.
G01N 21/35 (2014.01)
G01N 21/65 (2006.01)
G01N 21/3581 (2014.01)
G01N 21/3563 (2014.01)

(52) U.S. Cl.
CPC ......... *G01N 21/65* (2013.01); *G01N 21/3581* (2013.01); *G01N 21/3563* (2013.01)

(58) Field of Classification Search
CPC .......... G01N 21/3581; G01N 21/3586; H03B 2200/0084
See application file for complete search history.

(56) References Cited

U.S. PATENT DOCUMENTS

| 6,335,625 | B1 * | 1/2002 | Bryant et al. ................. 324/637 |
| 2004/0065831 | A1 * | 4/2004 | Federici ............. G01N 21/3581 250/341.1 |
| 2006/0214107 | A1 * | 9/2006 | Mueller ............. G01N 21/3581 250/341.8 |

* cited by examiner

Primary Examiner — Casey Bryant
(74) Attorney, Agent, or Firm — Wayne Edward Ramage; Baker Donelson

(57) ABSTRACT

A method and apparatus for remotely detecting, locating, and identifying chemicals and chemical compounds through optically opaque materials. Electromagnetic radiation in the Terahertz range emitted from an antenna array is modulated to excite target molecules. The apparatus then stops the excitation energy and the molecules emit an electromagnetic signature detectable by the device at standoff distances.

19 Claims, 9 Drawing Sheets

STIMULATED EMISSION AND ENHANCED DETECTION OF CHEMICALS AND CHEMICAL COMPOUNDS

This application is a continuation-in-part of U.S. patent application Ser. No. 13/585,322, now issued as U.S. Pat. No. 8,686,366, filed Aug. 14, 2012, which is a continuation of U.S. patent application Ser. No. 12/344,246, now issued as U.S. Pat. No. 8,242,450, filed Dec. 25, 2008, which claims priority to U.S. Provisional Patent Application No. 61/016,756, filed Dec. 26, 2007, entitled "Stimulated Emission and Enhanced Detection of Chemical Compounds," and is entitled to those filing dates for priority. The complete disclosures, specifications, drawings and attachments of U.S. patent application Ser. Nos. 13/585,322 and 12/344,246 and U.S. Provisional Patent Application No. 61/016,756 are incorporated herein in their entireties by specific reference for all purposes.

FIELD OF INVENTION

The present invention relates to methods and apparatus for remotely detecting, locating, and identifying chemicals and chemical compounds.

BACKGROUND OF INVENTION

A major challenge confronting military units and hazardous materials response teams involves the accurate and rapid identification of organic or inorganic chemicals outside the typical laboratory environment and under potentially dangerous conditions. Extreme care is required when analyzing unknown chemicals because of the possible instability of samples. Many chemicals can be sensitive to shock, heat, or light and could react violently including deflagration or explosion. In many cases, determining the nature of the unknown materials, whether biological (microorganisms) or chemical, is important and will dictate the handling, cleanup, disposal, and resolution of military or civilian issues.

Addressing the need for rapid and accurate analysis of samples that are suspected to be dangerous has been difficult for most current commercial analytical instruments available to military personnel and law enforcement field agents, especially given the fact that analysis may prove lethal if handled incorrectly. Many previous efforts to provide remote detection or identification have met with limited success. Radar-style imaging methods as described in U.S. Pat. Nos. 6,243,036, 6,359,582, and 7,205,926, and U.S. Patent Application Number 2005/0099330 demonstrated object detection at a distance; however, those inventions could not identify chemicals and chemical compounds. Raman and infrared (IR) spectroscopy methods as described in U.S. Pat. Nos. 5,112,127 and 7,301,148 demonstrated chemical compound identification: however, they were limited by sample preparation, strong IR absorbers like water, CO2, and glass (silica), and they required close or direct contact with the sample. U.S. Pat. Nos. 5,112,127, 6,243,036, 6,359,582, 7,205,926, and 7,301,148, and U.S. Patent Application Number 2005/0099330, are incorporated herein in their entireties by reference for all purposes.

Thus, what is needed is a method and apparatus for remotely detecting, locating, and identifying chemicals and chemical compounds at a safe standoff distance that does not require sample preparation and is not limited by strong IR absorbers or containers.

SUUMARY OF THE INVENTION

The present invention achieves detection and identification by means of molecular excitation. In one exemplary embodiment, the method of detecting and identifying chemicals and chemical compounds includes the steps of Stimulated Emission and Enhanced Detection (SEED). This method is initiated by the generation of a high power terahertz (THz) carrier wave signal. A sweep frequency generator modulates the THz carrier wave's frequency over a spectral segment that will excite the molecular composition of target materials which may be explosives, toxins, or other chemicals or chemical compounds. A modulated THz signal is fed through a waveguide, then amplified and emitted through an antenna.

The modulated THz radiation, as a function of an excitation interactive process with chemical and chemical compounds within a material, toggles the energy states causing a transition of energy states to occur in a predetermined manner for any resonate chemical or chemical compound. The collapse of energy from a high state back to ground (low) state causes the energy stored in the higher state to be released as electromagnetic radiation during the downward transition.

An antenna captures the emitted excitation electromagnetic radiation and feeds the radiation signal to a detector that is controlled by a dedicated Digital Signal Processor. The dedicated digital signal processor captures the signal decodes the signal and, analyzes the molecular structure as a function of the captured signal data compared to the modulation algorithm. That information is transmitted to the main computer where it is compared to a data base of known chemical excitation properties (in one exemplary embodiment, explosive chemical compounds, including, but not limited to, RDX, also known as Hexogen, Cyclonite and Cyclotri-methylene Trinitramine), together with the collected database stored in the main computer.

When a response from an explosive material is detected, the main compute signals a lock-on condition that generates an interrogative cycle between the sweep generator frequency excitation process and the main computer. Embodiments of the invention makes particular use of SEED to provide longer standoff distances while avoiding the adverse impacts of atmospheric disturbances.

DETAILED DESCRIPTION OF EXEMPLARY EMBODIMENTS

Figure 1:
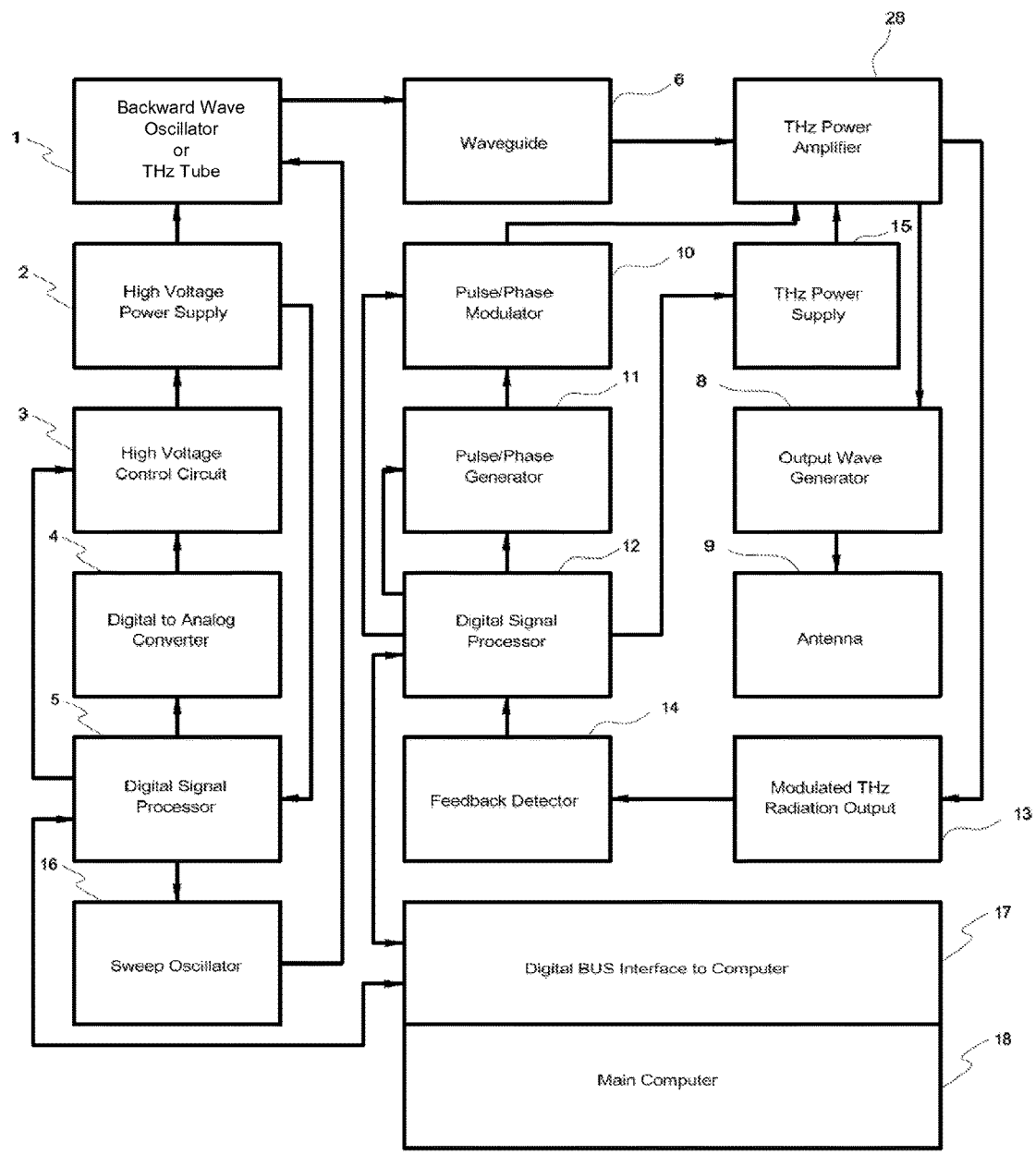
FIG. 1 is block diagram of an excitation generator in accordance with one embodiment of the present invention.
Figure 2:
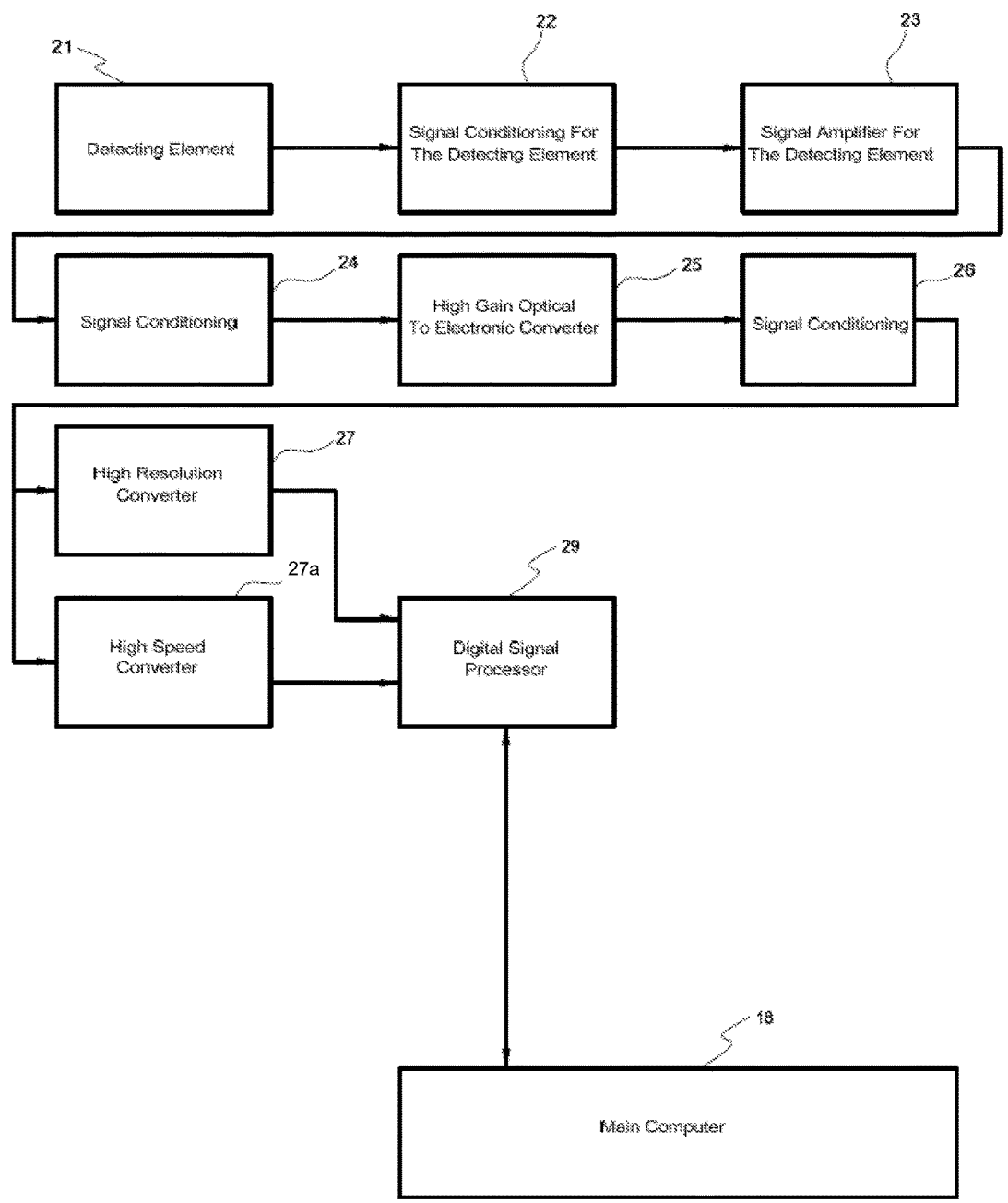
FIG. 2 is a diagrammatic representation of a detector system in accordance with an embodiment of the present invention.

The design of a practical detection system is predicated upon accepted theoretical principles of atomic-molecular absorption and emission which have been verified by experimental evidence. This detecting technology is also based on the principle that the emission of radiated energy, as a function of particle excursion between energy levels, is enhanced by an incident electromagnetic radiation upon the target molecular structure. That emitted radiation, which is obtained as a result of the stimulated energy level transitions at the molecular level, assumes an increased current density, which allows the explosive chemical to emit electromagnetic radiation, which can be detected by special high sensitivity detecting electronics. Although the detection system was designed especially for the early detection of improvised explosive devices (IEDs) carried by humans (HIEDs) or IEDs set up remotely at roadside, or IEDs that are concealed by optically opaque devices, enclosures or coverings, the system can be applied to analyze all molecular structures whether solid, liquid or in the vapor/gas phase. The emitted electromagnetic radiation that obtains from the incident radiation upon the molecular structure is referred to herein as secondary radiation.

The primary emission is the incident radiation. The process is a closed loop function and is referred to here as SEED, which refers to Stimulated Emission and Enhanced Detection. The incident radiation is in the THz spectrum and is utilized in such a way as to elicit secondary emission.

At normal temperatures molecules are either in their ground state or in their low-lying excited states. If an incident radiation presented to the atomic-molecular structure is large with respect to the size of the structure (nucleus) scattering occurs. The scattering which occurs, in this particular case, can be described in terms of classical electromagnetic theory. This particular scattering is referred to as Rayleigh scattering. The probability of Rayleigh scattering varies inversely as the fourth power of the wavelength ($\rho_\lambda = 1/\lambda^4$) and thus increases with the fourth power of frequency ($\rho_f = f^4$). Various other scattering principles are applied in the detection methodology described herein.

Electromagnetic radiation refers to the composite transmission of a mutually perpendicular electric and magnetic fields of some relative energy. Energy in the electromagnetic field is comprised of discrete units, which have been described as photons. When an electromagnetic field is incident on a molecule most of these photons are elastically scattered, having the same energy and wavelength as the incident photons. But about one photon out of every $10^7$ (ten million) photons are inelastically scattered and produce wavelengths that are different from the wavelength incident on the molecular structure; usually they are longer in wavelength than the incident ray. That process which describes inelastic scattering is referred to here as RAMAN SCATTERING. Raman scattering can occur with a change in the vibrational, rotational or electronic energy of a molecule. The difference between the energy of the incident photon and the Raman photon is equal to the vibrational energy of the scattering molecule.

The Raman spectrum is constructed from the intensity of the scattered emission compared to the energy difference. Several embodiments of the present system utilizes RAMAN SCATTERING. Thus, when the incident photon interacts with the electric dipole of the molecule, the resulting emissions constitute the Raman Effect.

In terms of classical physics, that interaction would be described as a perturbation of the molecular electric field. However, in quantum physics, the Raman scattering effect refers to the effect of a particle excursion to an altered state of excitation energy; thus having coincident lower excitation with a change in vibrational energy that corresponds to the energy differential.

Raman scattering, therefore, applies directly to embodiments of the present invention for the early detection of improvised explosive devices (IEDs). The general principles of Rayleigh and Mie scattering also apply to some extent and are presented for continuity and clarity of explanation. The quantum discussion as well as the classical discussion, here, is important to understanding the theoretical basis for the claimed methodology of early detection.

The discussion begins by recognizing that Raman scattering refers to inelastic scattering. However, both inelastic scattering and elastic scattering are germane to the present discussion. Inelastic scattering occurs when the incident photon has sufficient kinetic energy to cause an atom to transition from a lower state of excitation energy to a higher state of excitation energy. Elastic scattering occurs when the target molecule has sufficient mass as to appear as though infinite with respect to a projectile particle. The energy of the scattered photon is related to the incident energy of the photon which is given in terms of hf where: $hf' = hf - \Delta E$, and where $\Delta E$ is the excitation energy that describes the difference between the higher excitation state and the ground state; h is Plank's constant and f is frequency. The energy and, therefore, the frequency or wavelength of the scattered radiation is altered as the radiation either imparts rotational or vibrational energy to the scattering molecules or subtracts energy.

The line spectrum of the scattered emissions will have one prominent line corresponding to the original wavelength of the incident radiation and additional lines on each side of it. These additional lines correspond to the shorter or longer wavelengths of the altered portion of the radiation spectrum. It is this Raman spectrum that is characteristic of the transmitting molecular substance (the molecular structure). It is particularly useful for the signature characterization of materials, which is determined by this design, in addition to the detection and confirmation of an explosive material.

The iterations of the absorption-emission process described here are sometimes referred to as "Resonance Absorption." As an atom transitions from a higher energy state to a lower energy state the resulting emission of photons is referred to as spontaneous emission. This applies directly to various embodiments of the early detection methodology discussed in this document.

It is the current density of the emissions that is intentionally increased with the SEED methodology for purpose of detection. The increased current density facilitates higher signal to noise ratio and thus a more efficacious detection and reception process.

Referring now to the figures, wherein like references identify like elements of the invention, FIG. 1 illustrates an exemplary embodiment of the invention. A THz power tube or a backward wave oscillator functioning as a THz oscillator (i.e., a generator of an THz electromagnetic emission) 1 establishes the conditions for excitation of the target molecular compounds. It is powered by the high voltage circuit 2. A power supply, depicted in FIGS. 3B, 4, 5A and 5B, output affects the wavelength and amplitude of the THz tube or backward wave oscillator 1. In one embodiment, the THz tube comprises a vacuum tube reflex klystron oscillator, as described in Manohara, et al. "Design and Fabrication of a THz Nanoklystron," a copy of which is attached hereto and incorporated herein for all purposes as an appendix to this specification.

In order to amplify the THz signal generated by the THz tube or backward wave oscillator 1, a waveguide 6 may be necessary to propagate the low level oscillator signal to the excitation amplifier 28. An excitation amplifier 28 produces a high power THz emission that mitigates atmospheric aberration that would normally limit effective range. Therefore, the efficacy of the excitation is a function of output power by the THz amplifier. Since the THz wavelengths are short enough to be highly directional, a mechanical sweep of the antenna 9 will locate randomly placed chemical and chemical compounds. In one embodiment of the invention, a Horn antenna 9 is swept across a field of motion to excite randomly located molecules, whereupon the detection results from the collapsing energy state of the molecular compound back to its ground state.

Figure 6:
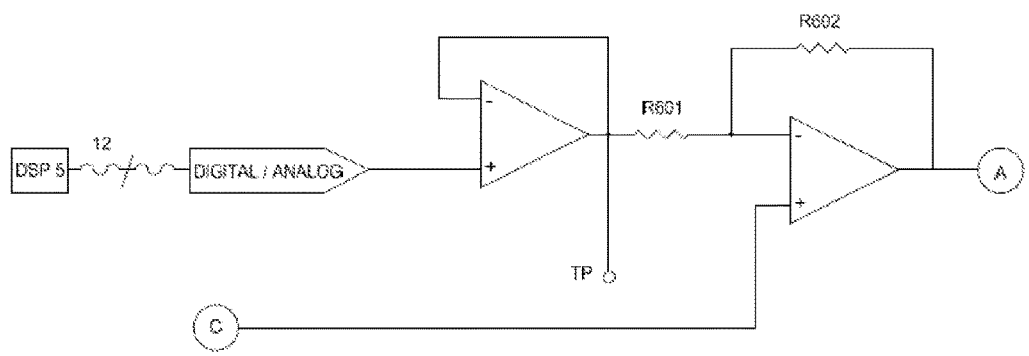
FIG. 6 is a diagrammatic representation of a digital/analog converter in accordance with an embodiment of the present invention.
Figure 7:
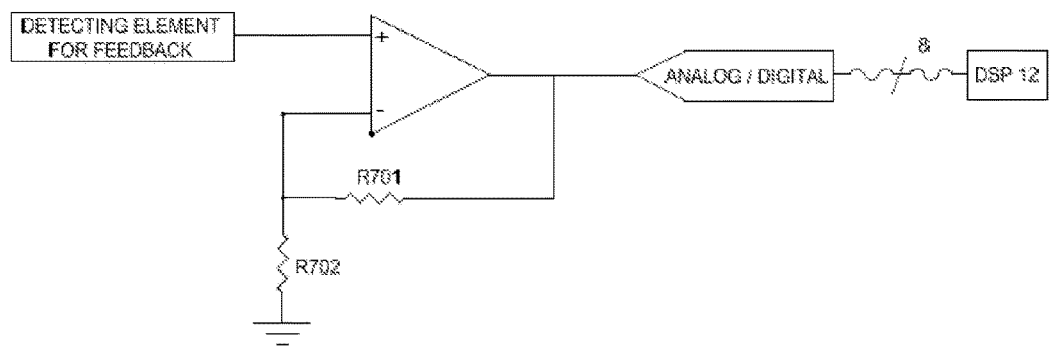
FIG. 7 is a diagrammatic representation of an analog/digital converter in accordance with an embodiment of the present invention.
Figure 8:
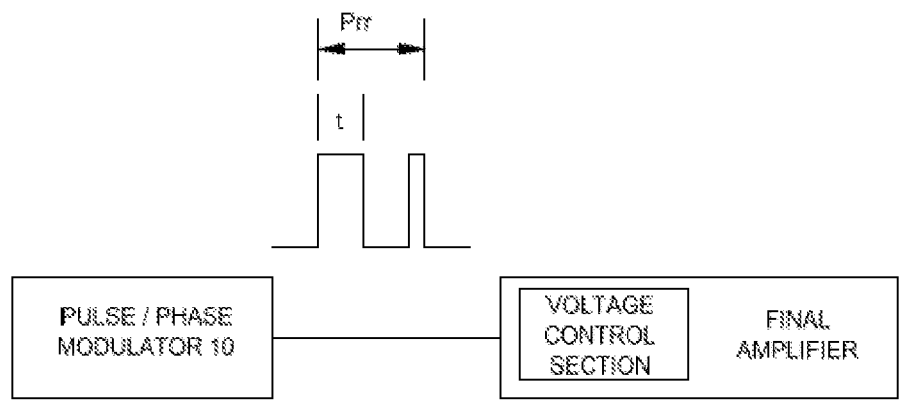
FIG. 8 is a diagrammatic representation of a pulse phase modulator in accordance with an embodiment of the present invention.

The excitation of target molecules depends not only on the output power of the THz signal but also on the modulation, which is utilized to find resonance with the molecular transitions as well as the inherent molecular resonance. In one embodiment, the modulation is accomplished by the operation of modulated THz radiation output 13, a feedback detector 14, a digital signal processor 12, a pulse/phase generator 11, and a pulse/phase modulator 10 as depicted in FIG. 1. In several embodiments, as shown in FIGS. 1 and 6, the modulation is a critical factor and unique to this invention. It is a method by which resonance with the molecular compound is achieved. The repetition rates and the pulse width and the phase angle of a sinusoidal emission are developed to resonate with the sub harmonics and transition states of the molecular compound.

In some exemplary embodiments, a main computer 18 is a host manager that delegates the actual real-time operation down to digital signal processors 5, 12. The main computer 18 performs database management which allows the dedicated digital signal processors 5, 12 to perform at higher speeds.

Figure 3A:
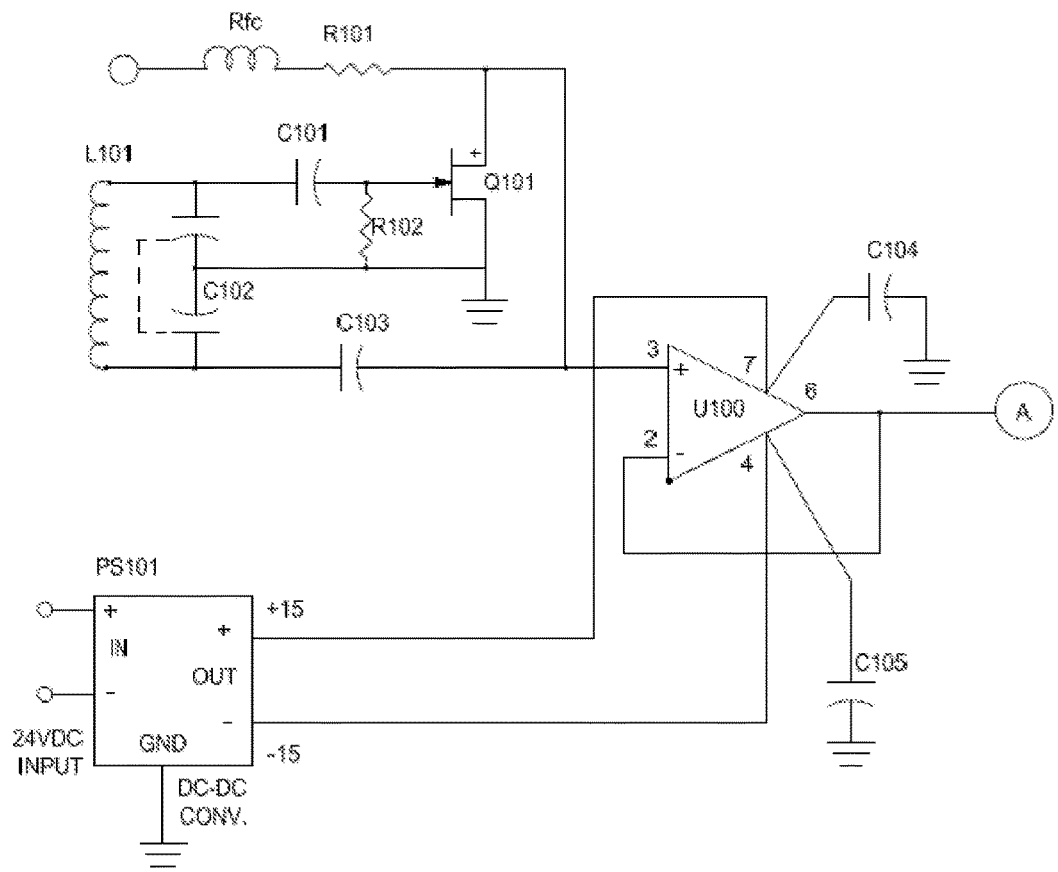
FIGS. 3a and 3b are circuit diagrams for a high voltage driver for an excitation amplifier in accordance with the present invention.
Figure 3B:
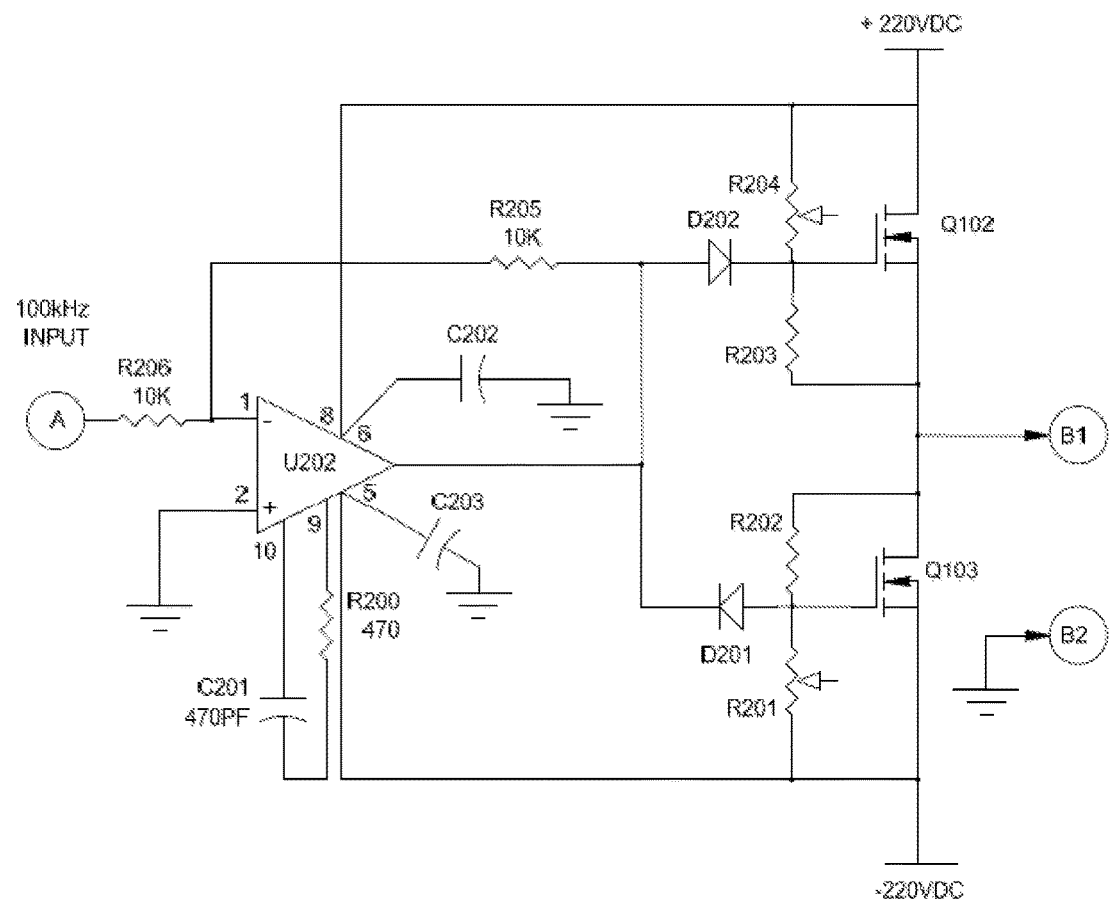
Figure 4:
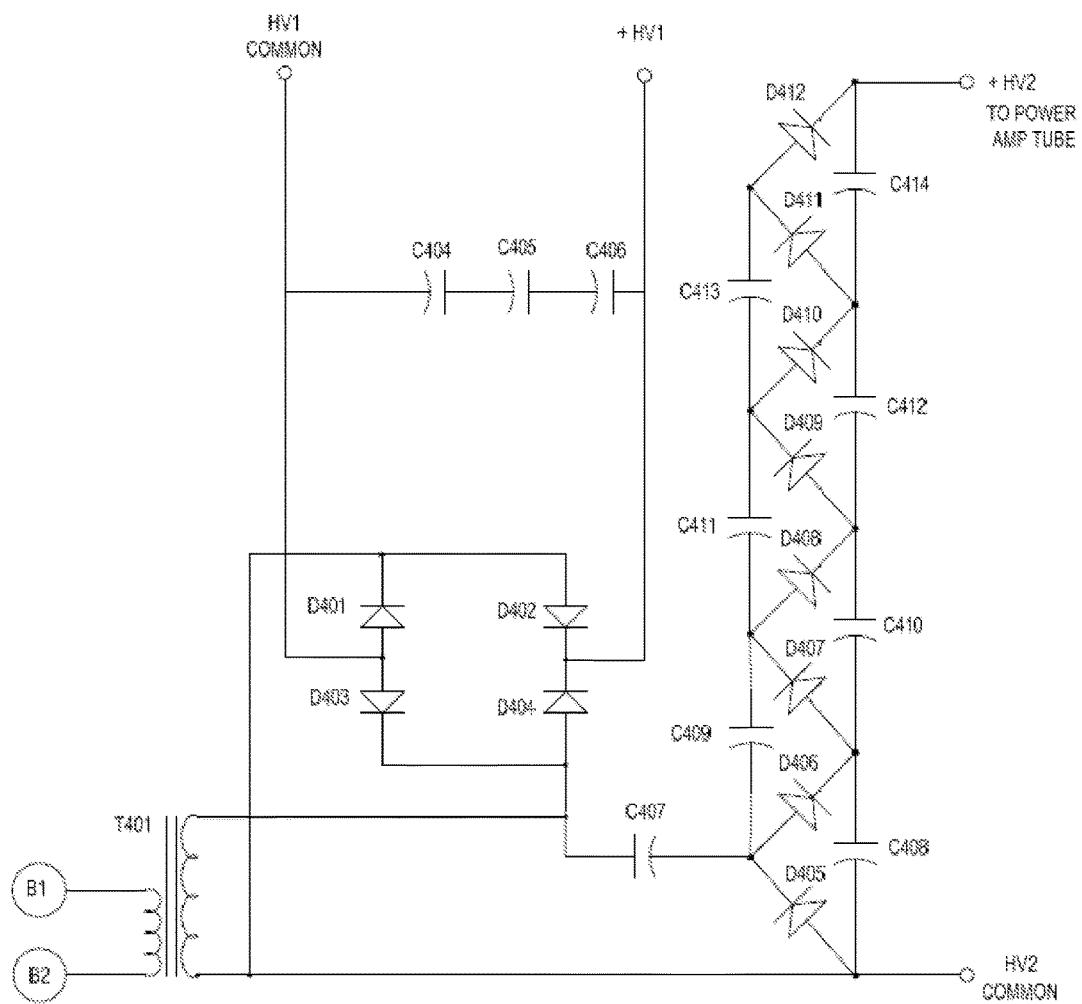
FIG. 4 is a circuit diagram for a high voltage multiplier with AC/DC converter in accordance with the present invention.
Figure 5A:
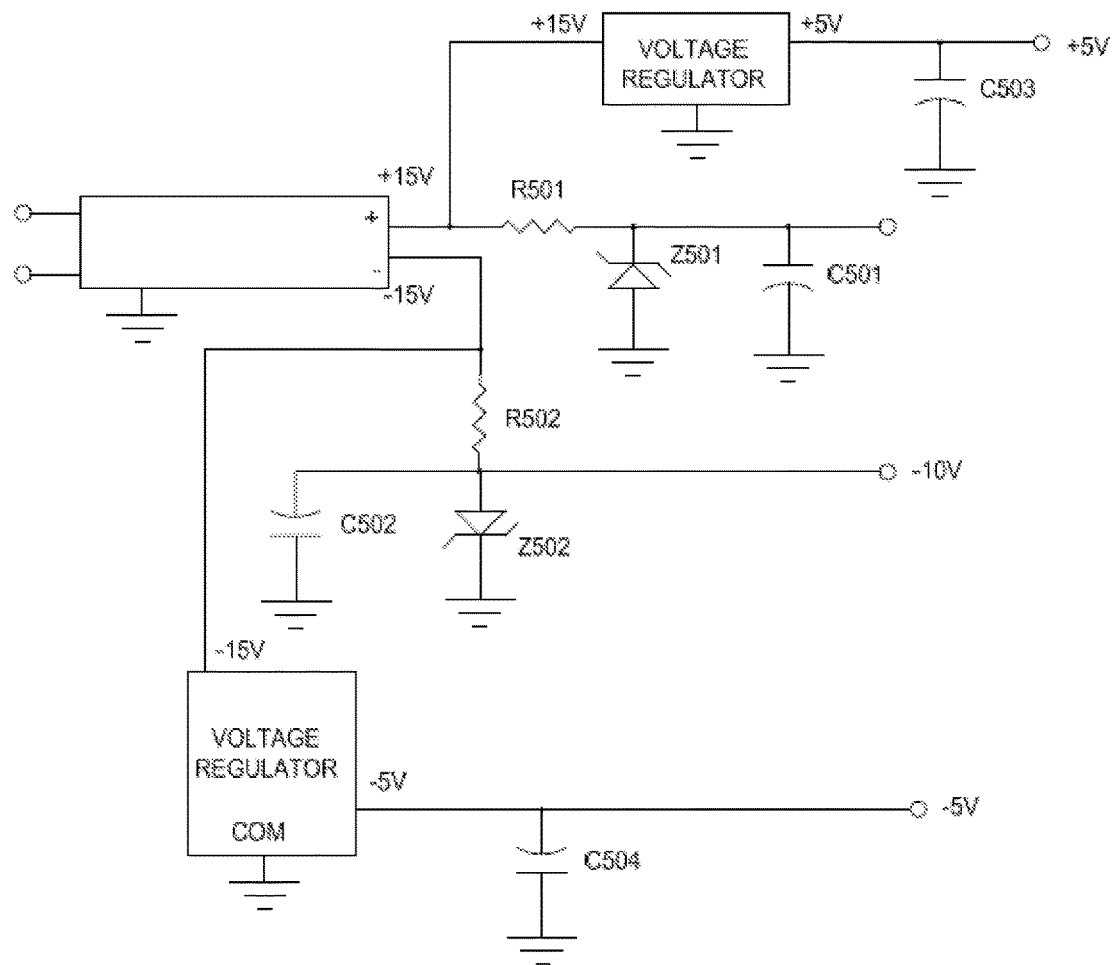
FIGS. 5a and 5b are circuit diagrams for a 100 kHz generator for backward wave oscillation in accordance with the present invention.
Figure 5B:
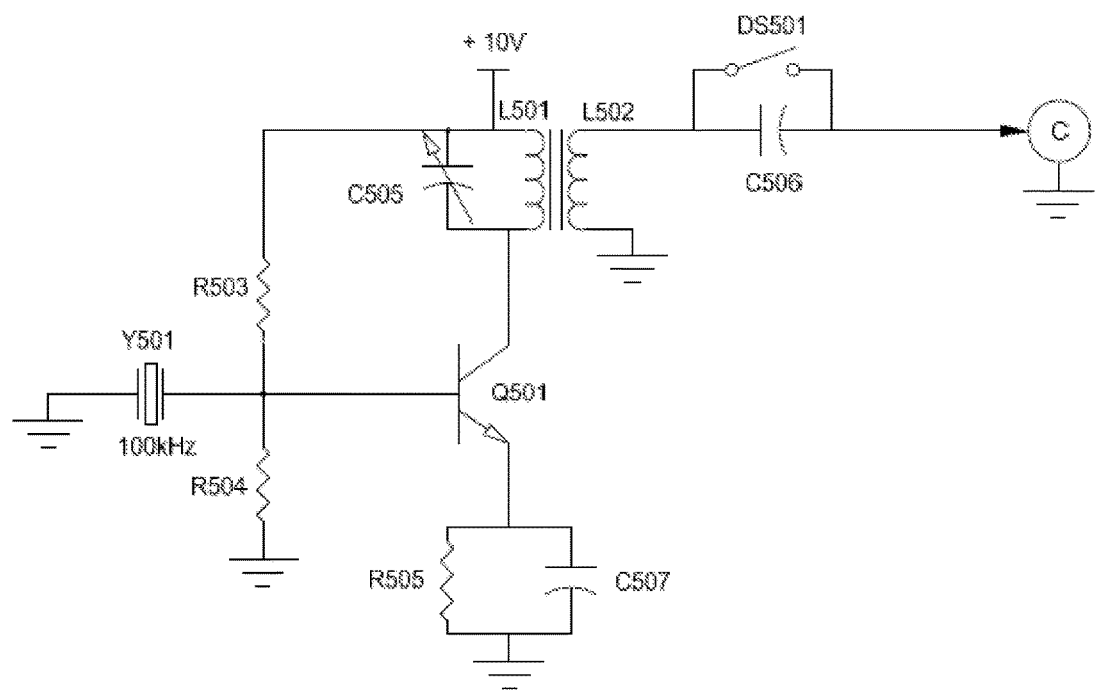

In another embodiment, a power amplifier 28 requires a high voltage, high current power supply. A THz power supply 15 powers both the THz tube or backward wave oscillator 1 and the power output tube of the THz power amplifier 28. A common transformer T401 supports two rectifier circuits depicted in FIG. 4. The first rectifier circuit comprises a plurality of diodes D401-D404 and capacitors C404-C406 connected as shown. Posts HV1 common and HV1+ apply to the THz tube or backwards wave oscillator 1. The second rectifier circuit comprises a plurality of diodes D405-D412 and polarized capacitors C407-C414 connected as shown. Posts labeled HV2 common and HV2+ apply to the power amplifier 28. The transformer T401 operates at 100 KHz. By increasing the operating frequency the magnetics are reduced substantially. Therefore the size and weight of the power supply are reduced also. A series of circuits depicted in FIG. 3A (comprising resistors R101-R102, polarized capacitors C101-C105, and inductor L101), FIG. 3B (comprising resistors R200-R206, polarized capacitors C201-C203, and transistors Q102-Q103), FIG. 5A (comprising resistor R501, polarized capacitors C501-C504, and Zener diodes Z501-Z502), FIG. 5B (comprising resistors R503-R504, polarized capacitors C506-0507, variable capacitor C505, switch DS501, transistor Q501, and inductors L501-L502), and FIG. 4 allow the power supplies to operate at 100 KHz instead of 60 Hz.

The power output is controlled in a closed loop fashion according the algorithms in a digital signal processor 12 and also by the feedback loop configured by the digital signal processor 12, a modulated THz radiation output 13, a feedback detector 14, and a THz power supply 15.

In this embodiment, the main computer 18 will initiate as much iteration as needed to confirm the valid detection of a molecular compound and assess its characteristic properties. In general, the detector system comprises a detecting element 21 with signal conditioning 22 and amplification 23. Signal conditioning 24, 26 is performed at several points, along with high gain optical to electronic conversion 25. A digital signal processor 29 receives input from the high resolution converter 27 and high speed converter 27*a*. The data collected by the main computer 18 is added to the database in order to build a table of properties relating to the molecular compounds analyzed. The information is compared to a table of RAMAN spectral data.

In the case of buried or optically obscured chemicals or chemical compounds, primary detection rests on the THz carrier because IR is constrained by the principles of optics. In laboratories and other such places the application of RAMAN spectroscopy becomes efficacious due to the advantage of close proximity and humidity control. The application of RAMAN spectroscopy for analysis is feasible and is included instrumentally in the apparatus described herein.

The diversity of TED tactical circumstances, especially related to techniques to obscure detection strongly suggests the use of THz for all possible scenarios. The problem of excitation at standoff distances by this method together with the modulation and appropriate power enables practical early detection. This method facilitates the process of stimulated emission, which is also referred to as secondary emission in this document.

When the molecular structure is alternately excited and collapsed by oscillating excitation pulses, determined according to the modulation algorithm, emission from the excited-ground state transitions must be sufficient for practical detection. To facilitate detection the specific circumstances of the emission to be detected must be resolved. The emission of interest will be electromagnetic radiation at some defined spectral segment in either the infrared spectrum or the terahertz spectrum or both, and at some very low level of intensity. The level of intensity is a major concern since normal emission intensities are of insufficient amplitude to be detected at any significant distance, and they are obscured beneath the noise amplitudes. Therefore, normal stimulated emission amplitudes are impractical for detection.

Increasing the amplification factor of the detecting system will also increase the noise amplitude, thus retaining the original problematic signal to noise ratio (SNR) making detection impractical. What is required is (1) sufficient signal amplitude for remote detection, and (2) a favorable signal to noise ratio prior to detection. The amplitude of the stimulated emission is not entirely a function of the power applied to the excitation process but rather a function of the current density of the emission itself, which is determined by the transition of energy states and the molecular structure. By modulating the excitation in such a way as to modify the rate of change of energy states with respect to time, one thus increases the total current density of the emission.

Since current density is a function of the excursion between energy levels (Δε), a given current density per transition (Δε) can be defined. The modulation yields f(i) =∫f(ε)·di. The total area under the curve represents current density. By this method, the current density of the stimulated emission is increased by remote methods. Thus, the SNR is also increased significantly by increasing the current density and, therefore, the signal amplitude is increased beyond the noise amplitude. There is, of course, a maximum amplitude level of current density that is uniquely associated with a given molecular structure. A distribution of maximum attainable current densities for a given set of molecular configurations can be constructed.

Once detection has been captured the objective is how to discern the emission of interest from some spurious emission. There must be certitude regarding the detection of an IED.

The function here is closed loop processing. A modulation algorithm transmitted is compared with a detected algorithm for agreement for this purpose. For example, if a series of transmissions for excitation are followed at intervals with some function, say 977MOD(X)+135MOD(Y)=N, the system will determine that N is, say 6, for instance, and the capture will be valid. Any other number besides 6 will reject the capture as a spurious reception.

More accurately, one says f(u)MOD(u)+f(v)MOD(v)=N. However, the process is rapidly iterated and a voting scheme similar to that used in fighter jets and spacecraft is employed. Achieved thereby is (1) excitation of the explosive material, (2) improved detectability by increasing the current density of the stimulated emission, and (3) determination of a valid or non-valid conditional response.

Various embodiments of the present invention thus can be used to detect, locate, and identify chemicals and chemical compounds including but not limited to explosive molecular compounds such as those used in IEDs. It may also be used to detect, locate, and identify organic and inorganic explosives including precursors, chemical warfare agents including precursors, pesticides, narcotics, solvents, and naturally occurring toxins to include the examination of materials having inhomogeneous compositions. Embodiments of the invention makes particular use of SEED to provide longer standoff distances while avoiding the adverse impacts of atmospheric disturbances. Depending on the configuration of the elements described herein, the standoff distance can be 10 meters, 25 meters, 50 meters, 100 meters, 250 meters, or greater.

Thus, it should be understood that the embodiments and examples have been chosen and described in order to best illustrate the principals of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. An apparatus to detect target material or materials in a device, object, area or location, comprising:
    a generator to generate a THz electromagnetic emission;
    a modulator configured to generate a modified THz electromagnetic emission by modulating the THz electromagnetic emission from the generator;
    an antenna to direct the modified THz electromagnetic emission towards a device, object, area or location that may contain target material or materials with molecules alternately subject to excitation when exposed to the modified THz electromagnetic emission; and
    a detector to detect signature emissions of excited molecules in the target material or materials;
    wherein the modified THz electromagnetic emission is configured to increase current density of the signature emissions.

2. The apparatus of claim 1, further wherein said modulator is configured to modulate the frequency of the THz electromagnetic emission over the frequency spectrum of the target material or materials.

3. The apparatus of claim 2, wherein the modulator is a sweep frequency generator.

4. The apparatus of claim 2, further comprising a computer, said computer analyzing detected signature emissions.

5. The apparatus of claim 4, further comprising one or more digital signal processors in communication with said computer.

6. The apparatus of claim 2, further comprising a feedback detector receiving the modulated THz electromagnetic emission.

7. The apparatus of claim 1, wherein the generator is a backward wave oscillator.

8. The apparatus of claim 1, wherein the generator is a THz tube.

9. The apparatus of claim 1, wherein the antenna is a horn antenna.

10. An method to detect target material or materials in a device, object, area or location, comprising:
    generating a THz electromagnetic emission;
    modulating the frequency of the THz electromagnetic emission over the frequency spectrum of a target material or materials with molecules alternately subject to excitation when exposed to the THz electromagnetic emission;
    directing the modulated THz electromagnetic emission towards a device, object, area or location that may contain said target material or materials;
    increasing emitted excitation electromagnetic radiation total current density from the device, object, area or location by remotely modulating the frequency of the THz electromagnetic emission; and
    analyzing said emitted excitation electromagnetic radiation from the device, object, area or location to detect signature emissions of excited molecules in the target material or materials.

11. The method of claim 10, wherein the THz electromagnetic emission is generated by a THz tube.

12. The method of claim 10, wherein the step of analyzing is performed by one or more digital signal processors.

13. The method of claim 10, further comprising the step of amplifying the THz electromagnetic emission.

14. A method to detect target materials, comprising the steps of:
    emitting electromagnetic radiation in the Terahertz range;
    modulating the electromagnetic radiation to alternately excite molecules in the target materials, resulting in signature emissions of electromagnetic radiation therefrom;
    remotely increasing the total current density of said signature emissions; and
    detecting signature emissions of alternately excited molecules in the target materials.

15. The method of claim 14, wherein the electromagnetic radiation is generated by a THz tube.

16. The method of claim 14, wherein the step of detecting is performed by one or more digital signal processors.

17. The method of claim 14, wherein detection is performed at a standoff distance of at least 10 m.

18. The method of claim 14, wherein detection is performed at a standoff distance of at least 25 m.

19. The method of claim 14, wherein detection is performed at a standoff distance of at least 50 m.

* * * * *